United States Patent [19]

Connor

[11] 4,108,889

[45] Aug. 22, 1978

[54] PREPARING ALKANE PHOSPHONIC ACIDS AND INTERMEDIATES

[75] Inventor: Daniel Stedman Connor, Cincinnati, Ohio

[73] Assignee: The Procter & Gamble Company, Cincinnati, Ohio

[21] Appl. No.: 743,186

[22] Filed: Nov. 19, 1976

[51] Int. Cl.$^2$ ................................................ C07F 9/38
[52] U.S. Cl. .......................... 260/502.4 R; 260/545 P; 260/683.2; 260/961; 260/971
[58] Field of Search ....................... 260/683.2, 502.4 R

[56] References Cited

U.S. PATENT DOCUMENTS

| | | | |
|---|---|---|---|
| 2,724,718 | 11/1955 | Stiles et al. | 260/502.4 R |
| 2,957,931 | 10/1960 | Hamilton et al. | 260/502.4 P |
| 3,064,031 | 11/1962 | Zimmerer | 260/461 |
| 3,151,179 | 9/1964 | Kennedy et al. | 260/683.2 |
| 3,316,331 | 4/1967 | Sims | 260/502.4 R |
| 3,351,558 | 11/1967 | Zimmerer | 252/137 |
| 3,370,101 | 2/1968 | Hayes et al. | 260/671 |
| 3,579,604 | 5/1971 | Tamolo | 260/666 |
| 3,600,475 | 8/1971 | Schimmelschmidt et al. | 260/970 |
| 3,812,222 | 5/1974 | Kleiner et al. | 260/970 |

FOREIGN PATENT DOCUMENTS

| | | | |
|---|---|---|---|
| 2,441,783 | 3/1976 | Fed. Rep. of Germany | 260/502.4 R |
| 2,441,878 | 3/1976 | Fed. Rep. of Germany | 260/502.4 R |

OTHER PUBLICATIONS

"Amberlyst is Synthetic Resin Catalyst", Technical Bulletin of the Rohm and Haas Company.
Gefter et al. "Plast. Massy" (1961), pp. 63-64.
Kosolapoff, "Organophosphorus Compounds" (1950), p. 139.

*Primary Examiner*—Joseph E. Evans
*Attorney, Agent, or Firm*—Robert B. Aylor; Richard C. Witte; Thomas H. O'Flaherty

[57] ABSTRACT

Preparation of long chain alkane phosphonic acids involves reacting alpha olefin with macroreticular strong acid cation exchange resin to isomerize the olefin, reacting resulting internally unsaturated olefin with dimethylphosphite to produce non-terminally substituted alkanephosphonic acid dimethyl ester, and demethylating with anhydrous hydrogen chloride or hydrogen bromide.

7 Claims, No Drawings

PREPARING ALKANE PHOSPHONIC ACIDS AND INTERMEDIATES

BACKGROUND OF THE INVENTION

This invention in one aspect relates to preparing non-terminally substituted alkane phosphonic acids. These acids are useful as detergent composition additives. (See Zimmerer U.S. Pat. No. 3,351,558 and Jacobsen Ser. No. 709,015 filed July 27, 1976, and now U.S. Pat. No. 4,070,309 and Jacobsen Ser. No. 728,579 filed Oct. 1, 1976).

This invention in another aspect relates to preparing internally unsaturated olefins (the term "internally unsaturated olefins" is used herein to mean olefins with unsaturation other than in the 1-position; it does not necessarily imply a thermodynamic equilibrium mixture; it does not include dimer and other telomers). Internally unsaturated olefins are useful as intermediates in the preparation of the non-terminally substituted derivatives in general as well as the alkane phosphonic acids specifically mentioned above.

Various methods of producing non-terminally substituted alkane phosphonic acids are known in the patent literature, but none of such methods is very suitable for a commercial process.

For example, the Zimmerer patent referred to above discloses a preparation involving reaction of a paraffin, phosphorus trichloride and oxygen followed by hydrolysis. One of the major problems associated with this preparation is production of product with a high percentage of phosphonate groups in the 1-position (approximately 16%). Another serious problem associated with this preparation is severe foaming in the hydrolysis step.

The Zimmerer patent also discloses a preparation involving isomerizing alpha olefin by use of iron pentacarbonyl and then adding phosphorous acid to the isomerized olefins using gamma radiation as a source of radicals. Major shortcomings of this preparation are the requirement of flammable and/or toxic solvents and the lack of availability of sufficient gamma radiation for commercial manufacture.

The Zimmerer patent also discloses a process involving radical addition of diisopropyl phosphites to internally unsaturated olefins followed by pyrolysis. There is a severe corrosion problem associated with the pyrolysis step of this process in relation to metal reaction vessels and an etching and corrosion problem in relation to glass lined metal vessels.

It is an object of this invention to provide a novel process for producing such acids where production of 1-phosphonates is minimized, where foaming does not occur, where usage of solvent is not required, where gamma radiation is not required, and where etching and corrosion problems are insignificant.

It is also an object of one embodiment of this invention to provide a novel process for isomerization of alpha olefins where conversion to internally unsaturated isomers is very high while dimer formation is minimized.

BRIEF DESCRIPTION OF THE INVENTION

The process herein is for producing non-terminally substituted alkane phosphonic acids where the alkane moiety is straight chain or branched and contains from 12 to 22 carbon atoms.

In general, such process involves three steps. The first step involves reacting alpha olefin with macroreticular strong acid cation exchange resin to isomerize the olefin (the term "isomerize" is used herein to mean convert to internally unsaturated olefin) under particular conditions of temperature and cation exchange resin moisture content. The second step involves reacting the internally unsaturated olefin with dimethyl phosphite to produce non-terminally substituted alkanephosphonic acid dimethyl ester wherein the alkane moiety contains from 12 to 22 carbon atoms. The third step involves demethylating the dimethyl ester with anhydrous hydrogen chloride or hydrogen bromide.

The above described preparation is represented by the following equations wherein $r\text{-}C_nH_{2n}$ stands for internally unsaturated olefin and $r\text{-}C_nH_{2n+1}$ stands for non-terminally substituted alkane moiety and $n$ ranges from 12 to 22 and X is chloride or bromide.

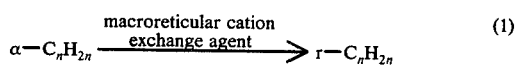

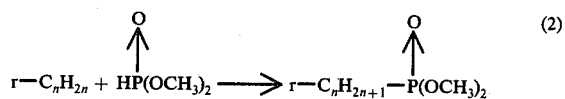

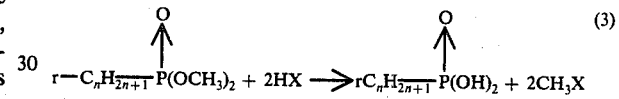

The first step is referred to herein as the isomerizing step. The second step is referred to herein as the diester forming step. The third step is referred to herein as the demethylating step.

The isomerizing step is believed to be novel. Selection and use of particular cation exchange resin moisture contents and particular reaction temperatures as described below is critical to converting alpha olefin to obtain high yields of internally unsaturated olefin while minimizing dimer formation, that is to converting at least about 98% of the alpha olefin (leaving less than about 2% by weight alpha olefin) to obtain product containing more than about 88% by weight internally unsaturated olefin, less than about 10% by weight dimer and the residual alpha olefin (less than about 2% by weight). The very high conversion to internally unsaturated olefin is important because residual alpha olefin, if not separated, when subjected to a diester forming step followed by demethylating, results in production of terminally substituted acids which are of restricted solubility whereby precipitation occurs on articles being treated with the detergent product. Restricting dimer formation is important because excess dimer, if not separated, when reacted in a diester forming step followed by demethylating to produce product used as a detergent additive, results in detergent product which is not effective for the intended purpose.

The diester forming step is believed to be novel. While several types of free radical initiators are possible to catalyze this reaction as described below, several chemical initiators are useful which are readily available commercially, and there is no necessity for resorting to gamma radiation. The selection of dimethylphosphite instead of other dialkylphosphites results in easily removed by-product (methyl chloride or methyl bromide) in the demethylating step.

The demethylating step is believed to be novel. The selection of anhydrous hydrogen chloride or anhydrous hydrogen bromide is important. With the use of anhydrous agents, there is no foaming. On the other hand the use of aqueous demethylating agents often results in severe foaming upon reaction to obtain high conversions, e.g. 80–95%, whereby the reaction mixture is not readily contained. Moreover, in this step, reaction can be carried out with acceptable results, in glass lined vessels or even in vessels of 316 stainless steel. Thus, this step is advantageous over the Zimmerer process described earlier involving pyrolysis where there are unacceptable etching and corrosion problems. Moreover, this step is advantageous over use of aqueous demethylating agents in relation to corrosion effect since reaction involving aqueous demethylating agents is highly corrosive to vessels of 316 stainless steel.

DETAILED DESCRIPTION OF THE INVENTION

We turn first of all to the isomerizing step.

The alpha olefin reactant is a straight chain or branched aliphatic olefin containing from 12 to 22 carbon atoms. A preferred alpha olefin is 1-octadecene. Other useful olefins are 1-dodecene, 1-tetradecene, 1-hexadecene, 1-eicosene, 1-docosene, 1-tridecene, 2-methyl-1-heptadecene, etc. Mixtures of alpha olefins of different chain lengths are readily used herein. The alpha olefins are obtainable commercially.

Cation exchange resins useful herein are of the strong acid type. They are used in the hydrogen form. They comprise a polymeric matrix, most commonly polystyrene cross-linked with divinylbenzene, and typically contain sulfonic acid functional groups. The resins herein are macroreticular resins. These are well known in the art. They have a macroporous character. More particularly, they have areas of microporous gel interspersed with macropores. The macropores are part of the rigid structure of each resin particle (bead). Reactants can move into the interior of the bead regardless of whether or not there has been solvent induced swelling. These resins have, for example, an internal surface area ranging from about 40 to about 600 square meters per gram, a porosity ranging from about 25 to about 60 volume percent and an average pore diameter ranging from about 50 to about 600 angstroms. A highly-preferred cation exchange resin is Amberlyst 15 which is obtainable from Rohm and Haas Company. Other suitable resins are Amberlyst XN-1005 and Amberlyst XN-1010 which are also obtainable from Rohm and Haas. Usually, the cation exchange resin is useful to process 50 to 250 or more times its own weight of olefin before it loses its effectiveness. The effectiveness of resin can be monitored by NMR or IR analysis for alpha olefin conversion and by GC analysis for dimer formation.

As indicated previously, the moisture content of the resin is critical to obtaining high levels of conversion of alpha olefin (conversion of at least about 98% of the alpha olefin, leaving less than about 2% by weight alpha olefin in the isomerized mixture) to obtain high yields of internally unsaturated olefin (more than about 88% by weight internally unsaturated olefin in the isomerized mixture) while avoiding dimer formation (less than about 10% by weight dimer in the isomerized mixture). Generally the moisture content ranges from about 3% by weight up to about 15% by weight, with from about 3% by weight to about 10% by weight being preferred.

The percent moisture referred to herein is taken as the weight loss after a sample of the resin has been maintained in a drying oven (no fan) for 18 hours at 105° C. If the lower limit on moisture content is not exceeded, reaction to obtain high conversion of alpha olefin results in excess dimer formation. If the upper limit on moisture content is exceeded, percentage conversion of alpha olefin is reduced to an unacceptable level even when a very long reaction time is utilized.

We turn now to methods of adjusting the moisture content of the resin. Resin may be obtained from the manufacturer in dry form (1 to 2½ percent moisture) or in wet form 20–25% moisture). The moisture content is readily adjusted to be within the general range described above or within the preferred range by wetting and/or drying procedures. Wetting is preferably carried out by a water soak. Wetting can also be carried out by a water/organic solvent soak. Drying is conveniently carried out in a rotary evaporator.

The weight ratio of olefin to resin used during reaction is uncritical and is mainly a matter of practicality. For example, the ratio can range from near zero (just a trickle of olefin over resin) to perhaps 100:1 for slow batch conversion.

Reaction solvents are not required in the isomerization step.

We turn now to the reaction temperature in the isomerization step. Generally, operative reaction temperatures range from about 80° to about 130° C, preferably from about 90° to about 125° C. Generally, lower temperatures are more useful when the resin is fresh, and preferably the low end of the temperature range is used when the resin is fresh, and progressively higher temperatures are used as the life of the resin becomes used up. In a very preferred embodiment, a temperature of 100° C is used when the resin is fresh, and progressively higher temperatures are used during the resin life up to 120° C. The temperature is readily controlled, for example, by use of a thermoregulator comprising a device which detects the mercury level in a thermometer and signals a heating mantle in response to rise or fall of such mercury level. If the above recited lower limit of about 80° C is not exceeded, percentage conversion is reduced to an unacceptable level or there is no isomerization at all. If the upper limit of about 130° C is exceeded, degradation of resin can occur (sulfonic acid groups are lost) and dimer formation can be excessive. The reaction is carried out so that there is no significant moisture change in the resin even when the higher temperatures in the above described range are utilized.

The isomerization step is readily carried out as a batch process or as a continuous process.

If a batch process is used, a suitable reactor consists of a flask equipped with a paddle stirrer, heating means, and means to control the temperature to within a preselected two-degree range. The reaction for a batch process is carried out for a time period sufficient to obtain the aforedescribed high conversion of alpha olefin. This time period ranges, for example, from about 1 to 10 hours, preferably from about 4 to about 6 hours, when the resin is fresh, and from about 3 to 30 hours, preferably from about 5 to 15 hours, later in the life of the resin. The batch reaction is preferably carried out under an inert gas blanket, preferably under a blanket of nitrogen. The batch reaction is preferably carried out under atmospheric pressure. The reactor preferably is one whereby moisture driven from the resin during reaction is condensed and returned to the resin; this happens automatically in the above described flask where condensation occurs at the unheated upper portion of the flask resulting in the condensation within the flask and condensate returning to the reaction mixture and the resin.

If a continuous process is used, the reactor can be a conventional column with the resin maintained on screen or filter structure with olefin entering the top and exiting the bottom. For a continuous reactor, typically flow rates ranging from one liter per kilogram of resin per hour to 30 liters per kilogram of resin per hour are used. The continuous process is preferably carried out at atmospheric pressure.

As previously indicated, the product of the isomerization step contains a very high percentage of internally unsaturated olefin and low alpha olefin and dimer content (more than about 88% by weight internally unsaturated olefin, less than about 2% by weight alpha olefin and less than about 10% by weight dimer). The product usually contains 10–25% by weight 2-position isomer, 10–40% by weight 3-position isomer, 10–25% by weight 4-position isomer and the remainder besides 1-position isomer and dimer being more internally unsaturated isomer (e.g., 5-, 6-, etc., position).

We turn now to the diester forming step (it is a phosphonation reaction).

The internally unsaturated olefin reactant is desirably provided by the isomerization reaction described above. The dimethylphosphite reactant is readily available commercially.

The diester forming (phosphonation) reaction is a free radical chain reaction. The olefin double bond undergoes an addition reaction initiated by the presence of free radicals in intimate contact with the reactants. The reaction is readily initiated by various common free radical initiators and preferably by chemical initiators. A highly preferred initiator is di-tert-butylperoxide. Other very suitable initiators are dibenzoylperoxide, azobisisobutyronitrile, and tert-butylperbenzoate.

Turning now to the reaction conditions, the mole ratio of dimethylphosphite to olefin useful in the reaction generally ranges from about 10:1 to about 1:1 with about 2:1 to about 4:1 being preferred. When di-tert-butylperoxide is the free radical initiator, the mole ratio of it to olefin useful herein ranges, for example, from about 0.01:1 to about 0.05:1, preferably from 0.02:1 to 0.03:1. No reaction solvent is required. The reaction is preferably carried out under an inert gas, e.g. nitrogen, atmosphere. The reaction temperature ordinarily ranges from about 60° to about 165° C. When di-tert-butylperoxide is used as the initiator, the reaction temperature preferably ranges from about 135° to about 145° C. The reaction time for a batch reaction ordinarily ranges from about one hour to about ten hours, preferably ranging from about three hours to about six hours. The reaction is readily carried out at atmospheric pressure. The reaction can be carried out, for example, in a stirred flask with a thermoregulator and heating mantle with all reactants being added initially. In this reaction, some dimerization occurs, for example up to about 10% of the olefin is converted to dimer in this reaction; this makes it especially important to utilize the hereinbefore described isomerizing reaction thereby restricting dimer formation in the isomerizing reaction.

We turn now to the demethylating step. The diester reactant is readily available as described above. The anhydrous hydrogen chloride and anhydrous hydrogen bromide reactants are readily commercially available. Anhydrous hydrogen chloride is preferred over anhydrous hydrogen bromide. When anhydrous hydrogen chloride is utilized as the demethylating agent, the reaction temperature ordinarily ranges from about 80° to about 160° C and preferably ranges from about 100° to about 140° C. When anhydrous hydrogen bromide is utilized as the demethylating agent, the reaction temperature ordinarily ranges from about 25° to about 120° C. The reaction time ordinarily ranges from about 1 hour to about 20 hours and preferably ranges from about 4 hours to about 8 hours. No reaction solvent is required. The reaction can be carried out at atmospheric pressure. Stoichiometric amounts of demethylating agent can be used up to, for example, a 3:1 equivalent excess. In this step, the anhydrous hydrogen chloride or hydrogen bromide functions to displace the methyl groups as methyl halides which readily distill from the reaction mixture. Sparging with excess demethylating agent aids in removing methyl halide by-product from the system. At atmospheric pressure and with no solvent being utilized, a sparge of 2:1 equivalent excess of anhydrous hydrogen chloride is sufficient to drive the reaction to greater than 99% completion. The reaction is readily carried out in a glass lined metal vessel (without etching or corrosion occurring) or in a vessel of 316 stainless steel (with corrosion being within acceptable limits - less than 20 milligrams per square decimeter per day). There is no foaming during the reaction.

The conditions described above for the demethylating step lead to some phosphonic acid anhydride formation (e.g. 5 to 10 atom percent; $^{31}$P NMR analysis). The anhydride is readily converted to acid as follows: The product from the demethylating reaction is transferred to a glass lined metal vessel or other suitably corrosion resistant vessel, if it is not already in such a vessel. It is then cooled, for example, to 90° C to 100° C. Then a small amount of water is added, for example, to provide a weight ratio of such product (the result of the demethylating reaction) to water ranging from about 400:1 to about 50:1, preferably ranging from about 250:1 to about 150:1. The resulting mix is stirred, for example for a time period ranging from 30 minutes to 2 hours at a temperature ranging from 90° to 100° C to thereby hydrolyze anhydride. A weight ratio of at least about 50:1 as described above is important to the avoidance of foaming in this hydrolysis reaction.

The following examples are illustrative of the scope of the invention and are not to be construed in any way as limiting the scope of the invention.

EXAMPLE I 30 grams of Amberlyst 15 (dry form) cation exchange resin (referred to above) is soaked in water overnight, decanted, rotary evaporated for 30 minutes, and dried in a 115° C oven for 2.5 hours. The resin is then used in a different run. Resin recovered from that run has a moisture content of about 5% by weight.

The 30 grams of resin and 300 milliliters of 1-octadecene are introduced into a flask equipped with a paddle stirrer, thermoregulator, and heating mantle. A static nitrogen atmosphere is provided in the flask over the reaction mixture. The reaction mixture is rapidly brought to 110° C and maintained at this temperature for 2½ hours, with stirring. The product is separated from the resin by decanting. In this reaction, conversion of alpha olefin is over 98% resulting in internally unsaturated olefin content greater than 93% by weight and dimer content of 4.4% by weight.

1510 grams (1910 milliliters) of product prepared as above (sulfur analysis 290 ppm), 1980 grams (1650 milliliters) dimethylphosphite and 20 grams (25 milliliters) di-tert-butylperoxide are introduced into a flask (the mole ratio of dimethylphosphite to olefin is about 3:1 and the mole ratio of free radical initiator to olefin is about 0.023:1). The temperature of the reaction mix is raised to 135° C and held there for 2 hours and then is raised to 140° C and held there for 4 hours. Nuclear magnetic resonance indicates the reaction is over 90% complete at the three-hour point. Workup consists of distilling off excess dimethylphosphite at 50° C/5mm.Hg. The volatile decomposition products of di-tert-butylperoxide are caught in a liquid nitrogen foretrap to the vacuum pump. The product is mainly (about 90 mole percent) non-terminally substituted octadecanephosphonic acid dimethyl ester; the remainder is mostly phosphonated ester dimer.

37 milliliters (approximately 0.1 mole) of the product prepared above consisting mainly of non-terminally substituted octadecanephosphonic acid dimethyl ester is added into a glass lined metal vessel and is heated to 140° C. Dry nitrogen gas is sparged through the material as it is being brought to 140° C. Then anhydrous (strictly dry) hydrogen chloride is sparged through. The reaction mix is maintained at 140° C for 5 hours. During that time a total of 15.1 grams (0.41 moles) dry hydrogen chloride is sparged or approximately a 2:1 equivalent excess. The off-gases, methyl chloride and excess hydrogen chloride, escape via a glass wool plugged condenser up a fume hood. NMR analysis of the reaction mixture is used to determine methyl ester content. After 3 hours, the reaction is 98.5% complete, and after 5 hours, the reaction is 99% complete. There is no foaming and no etching or corrosion. The reaction mixture is maintained in the same glass lined metal vessel and is cooled to 100° C. Then 0.15 milliliter of water is added (to provide a weight ratio of reaction mix to water of about 200:1 and stirring is carried out for 1 hour while the 100° C temperature is maintained, whereby anhydride is hydrolyzed to acid. There is no foaming in this hydrolysis reaction; there is no etching or corrosion of the vessel in this hydrolysis reaction. The resultant light yellow, somewhat viscous oil weighs 32 grams and is mainly non-terminally substituted octadecane phosphonic acid. It is suitable for use in a detergent product and the 1-phosphonate level is sufficiently low so there is no unacceptable effect due to such level. The dimer level is sufficiently low so that the product maintains a high active level.

When in the above example, macroreticular cation exchange agents of the strong acid type in the hydrogen form other than Amberlyst 15 are utilized, for example when Amberlyst XN-1005 or Amberlyst XN-1010 are substituted for the Amberlyst 15, results are obtained equal to those obtained above of high conversion of alpha olefin to internally unsaturated olefin with very low conversion to dimer.

When, in the above example, a 316 stainless steel vessel is used in the demethylating step, corrosion is within acceptable limits. The reaction mix resulting from the demethylating reaction is transferred to a glass lined vessel for hydrolysis of anhydrides unless residual hydrogen chloride is removed prior to such hydrolysis.

When, in the above example, anhydrous hydrogen bromide is substituted for the anhydrous hydrogen chloride in the demethylating step, demethylation is accomplished without foaming occurring, without corrosion problems and with easy removal of excess hydrogen bromide and by-product methyl bromide.

When in the above example, aqueous hydrochloric acid (e.g., 37% hydrochloric acid) is used in place of the anhydrous hydrogen chloride, severe foaming often results when reaction completeness approaches 80-95%, causing the reaction mix to bubble out of the reactor.

EXAMPLE II 30 grams of Amberlyst 15 having a moisture content of approximately 5% is reacted with 340 milliliters of 1-hexadecene, with stirring, at 110° C under a static nitrogen blanket. After 3.5 hours, conversion of alpha olefin is greater than 98% complete; internally unsaturated olefin content is greater than 94% by weight; and dimer content is only 3.3% by weight. The internally unsaturated olefin is readily converted to non-terminally substituted hexadecane phosphonic acid by phosphonating with dimethylphosphite and demethylating the resulting diester with anhydrous hydrogen chloride by the procedure described above.

EXAMPLE III 30 grams of Amberlyst 15 having a moisture content of approximately 5% is reacted with 273 milliliters of 1-tetradecene, with stirring, at 110° C under a static nitrogen atmosphere. After 1.5 hours at 110° C, the temperature is allowed to fall to 50° C in 0.5 hours. At this point, conversion of alpha olefin is greater than 98% complete; internally unsaturated olefin content is greater than 94% by weight, dimer content is only 3.3% by weight. The internally unsaturated olefin is readily converted to non-terminally substituted tetradecane phosphonic acid by phosphonating with dimethylphosphite and demethylating the resulting diester with anhydrous hydrogen chloride by the procedure described above.

EXAMPLE IV

About 10 grams of Amberlyst 15 (dry form) is soaked in 50 milliliters of ether saturated with water for one hour and rotary evaporated to remove ether. This procedure has the effect of adjusting the moisture content of the resin to about 5% by weight. 40 milliliters of 1-dodecene and 4 grams of the moisture adjusted resin are reacted, with stirring, at 110° C under a static nitrogen atmosphere. After one hour, the alpha olefin is essentially completely converted, and the resulting reaction product is essentially entirely internally unsaturated olefin except for 3.8% by weight dimer. The internally unsaturated olefin is readily converted to non-terminally substituted dodecane phosphonic acid by phosphonating with dimethylphosphite and demethylating the resulting diester with anhydrous hydrogen chloride by the procedure described above.

EXAMPLE V

Approximately 16 grams of Amberlyst 15 (dry form containing 1.35% moisture) having been weighed into an Erlenmeyer flask is covered with water and allowed to stand overnight. Bulk water is stripped from the sample with a rotary evaporator at 55°-60° C/10 mm.Hg. until the resin appears to be dry. The sample is then further dried by placing the Erlenmeyer flask in a 115° C drying oven. At two-hour intervals, the flask is allowed to cool in a desiccator and subsequently is weighed. This procedure is repeated four times. A moisture content of 7.11% is obtained.

4 grams of the moisture adjusted resin and 40 milliliters of 1-dodecene are introduced into a batch reactor and are maintained at 115° C with stirring. After 1.5 hours, NMR analysis indicates no detectable alpha olefin (indicating less than 1% alpha olefin) and GC analysis indicates 4.4% dimer by weight. Thus, the reaction produces product which is essentially entirely internally unsaturated olefin except for the 4.4% by weight dimer. The internally unsaturated olefin is readily converted to non terminally substituted dodecane phosphonic acid by phosphonating with dimethylphosphite and demethylating the resulting diester with anhydrous hydrogen chloride by the procedure described above.

When in the above Examples I-V, branched chain alpha olefins, for example 2-methyl-1-heptadecene or 2-methyl-1-undecene, are substituted for the straight chain alpha olefins used in the examples, results are obtained equal to those obtained in the examples, namely high conversion to internally unsaturated olefin with low dimer formation in the isomerization step and no foaming in the demethylating step, no etching or corrosion problem when using a glass lined vessel in the demethylating step and easy by-product removal in the demethylating step.

EXAMPLE VI 1-octadecene (300 milliliters) is treated with 30 grams of Amberlyst 15 (moisture content 2.29% by weight, with stirring) for 2 hours at 150° C. Conversion of alpha olefin is complete, and dimer content is 58% by weight. This example demonstrates that use of a reaction temperature above the upper limit of 130° C contributes to excess dimer formation.

EXAMPLE VII

Amberlyst 15 (dry form) is soaked for 0.5 hour in water, and then is decanted, and then is rotary evaporated for 0.5 hour at 60° C. The moisture adjusted resin has a moisture content of 21.6% by weight. Treatment of 400 milliliters of 1-octadecene with 40 grams of resin for 5.5 hours at 110° C gives no isomerization, thereby demonstrating the criticality of the upper limit of about 15% for resin moisture content. A nitrogen sweep is applied to the reaction mixture to lower the resin moisture content below 15%; isomerization is readily catalyzed by the moisture adjusted resin.

EXAMPLE VIII 40 grams of Amberlyst 15 (dry form containing 1.65% moisture by weight) is reacted with 400 milliliters 1-tetradecene with stirring at 115° C. After 1.5 hours, NMR analysis indicates no alpha olefin and GC analysis indicates 28% by weight dimer, thereby demonstrating the criticality of the lower limit of about 3% for resin moisture content.

The term "convert" is used herein in relation to alpha olefin to mean reaction to produce internally unsaturated olefins and dimer.

The invention may be embodied in other specific forms without departing from the essential characteristics thereof. In view of the variations that are readily understood to come within the limits of the invention, such limits are determined by the scope of the claims.

I claim:

1. Process for preparing long chain alkane phosphonic acids, said process comprising the steps of
   (a) reacting alpha olefin with cation exchange resin to convert at least about 98% of the alpha olefin to obtain high yields of internally unsaturated olefin while minimizing dimer formation, said alpha olefin being a straight chain or branched aliphatic olefin containing from 12 to 22 carbon atoms, said cation exchange resin being a macroreticular resin of the strong acid type in the hydrogen form and having a moisture content ranging by weight from about 3% to about 15%, said reaction being carried out at a temperature ranging from about 80° to about 130° C;
   (b) reacting resulting internally unsaturated olefin with dimethyl phosphite to produce non-terminally substituted alkanephosphonic acid dimethyl ester; and
   (c) reacting said dimethyl ester with anhydrous hydrogen chloride or anhydrous hydrogen bromide to displace the methyl groups as methyl halides.

2. Process as recited in claim 1, in which said alpha olefin is 1-octadecene.

3. Process as recited in claim 2, in which said cation exchange resin has a moisture content ranging by weight from about 3% to about 10% and in which the reaction of step (a) is carried out at a temperature ranging from about 90° to about 125° C.

4. Process as recited in claim 3, in which the reaction of step (c) is carried out utilizing anhydrous hydrogen chloride.

5. Process as recited in claim 1 wherein water is added to product resulting from step (c), to hydrolyze anhydride; the weight ratio of such product to such water exceeding about 50:1.

6. Process for preparing non-terminally substituted alkane phosphonic acid, said process comprising reacting non-terminally substituted alkane phosphonic acid dimethyl ester wherein the alkane moiety contains from 12 to 22 carbon atoms with a demethylating agent selected from the group consisting of anhydrous hydrogen chloride and anhydrous hydrogen bromide and water is added to product resulting from the reaction, to hydrolyze anhydride.

7. Process as recited in claim 6 wherein the weight ratio of such product to water added exceeds about 50:1.

* * * * *